(12) United States Patent
Hsu

(10) Patent No.: US 9,984,211 B2
(45) Date of Patent: May 29, 2018

(54) CLINICAL INFORMATION MANAGEMENT SYSTEM

(71) Applicant: MedicusTek, Inc., Taipei (TW)

(72) Inventor: Chia-Ming Hsu, Taipei (TW)

(73) Assignee: MedicusTek, Inc., Taipei (TW)

( * ) Notice: Subject to any disclaimer, the term of this patent is extended or adjusted under 35 U.S.C. 154(b) by 0 days. days.

(21) Appl. No.: 15/202,372

(22) Filed: Jul. 5, 2016

(65) Prior Publication Data

US 2016/0314270 A1 Oct. 27, 2016

Related U.S. Application Data

(63) Continuation of application No. 14/315,329, filed on Jun. 26, 2014, now Pat. No. 9,384,651.

(30) Foreign Application Priority Data

Dec. 18, 2013 (TW) .............................. 102146970 A

(51) Int. Cl.
| | | |
|---|---|---|
| *G08B 1/08* | (2006.01) | |
| *G06F 19/00* | (2018.01) | |
| *G08B 21/22* | (2006.01) | |
| *A61B 5/00* | (2006.01) | |
| *A61B 5/11* | (2006.01) | |
| *H04L 29/08* | (2006.01) | |

(52) U.S. Cl.
CPC .......... *G06F 19/3418* (2013.01); *A61B 5/002* (2013.01); *A61B 5/0022* (2013.01); *A61B 5/0077* (2013.01); *A61B 5/1117* (2013.01); *A61B 5/447* (2013.01); *A61B 5/4815* (2013.01); *A61B 5/6804* (2013.01); *A61B 5/6892* (2013.01); *A61B 5/7275* (2013.01); *G08B 21/22* (2013.01); *H04L 67/1097* (2013.01); *A61B 2562/0247* (2013.01); *G16H 15/00* (2018.01); *G16H 50/20* (2018.01)

(58) Field of Classification Search
CPC ............ A61B 2562/0219; A61B 5/002; A61B 5/0002; A61B 5/14551; A61B 5/0402; A61B 5/0816; A61B 5/6824; A61B 5/746; A61B 5/0205; A61B 5/02125; A61B 5/0809; A61B 5/113; A61B 5/01; A61B 5/021
USPC .......... 340/539.17, 556, 286.07, 521, 573.1, 340/573.7, 539.12, 539.11, 666, 665, 340/603–604
See application file for complete search history.

(56) References Cited

U.S. PATENT DOCUMENTS

| | | | | |
|---|---|---|---|---|
| 6,856,832 | B1 * | 2/2005 | Matsumura | .......... A61B 5/0006 128/903 |
| 9,384,651 | B2 * | 7/2016 | Hsu | ...................... G06F 19/3418 |
| 2005/0101844 | A1 * | 5/2005 | Duckert | ............... A61B 5/0002 600/300 |
| 2005/0272564 | A1 * | 12/2005 | Pyles | ................. A63B 22/0257 482/54 |

(Continued)

*Primary Examiner* — Daniel Previl
(74) *Attorney, Agent, or Firm* — Osha Liang LLP

(57) ABSTRACT

A clinical information management system including a patient sensor system that collects data of a patient, a hospital information system that displays the data, a clinical server that processes the data from the patient sensor system and determines whether the patient is in need of assistance, and a monitoring apparatus. The clinical server transmits a message to the monitoring apparatus based on the data.

27 Claims, 9 Drawing Sheets

(56) References Cited

U.S. PATENT DOCUMENTS

| | | | | |
|---|---|---|---|---|
| 2008/0147442 A1* | 6/2008 | Warner | ............. | A61G 7/018 |
| | | | | 705/3 |
| 2013/0128022 A1* | 5/2013 | Bose | ............. | H04N 7/18 |
| | | | | 348/77 |
| 2013/0245389 A1* | 9/2013 | Schultz | ............. | A61B 5/0002 |
| | | | | 600/301 |
| 2014/0039351 A1* | 2/2014 | Mix | ............. | A61B 5/1114 |
| | | | | 600/587 |
| 2014/0135603 A1* | 5/2014 | Boyer | ............. | A61B 5/002 |
| | | | | 600/324 |

\* cited by examiner

CLINICAL INFORMATION MANAGEMENT SYSTEM

CROSS-REFERENCE TO RELATED APPLICATIONS

The present application is a continuation-in-part application of U.S. patent application Ser. No. 14/315,329, filed on Jun. 26, 2014, which claims foreign priority to Taiwanese Patent App. No. 102146970, filed on Dec. 18, 2013. These applications are incorporated herein in their entirety by reference.

FIELD OF THE INVENTION

One or more embodiments of the invention relate to a management system. More specifically, one or more embodiments of the invention relate to a clinical information management system.

SUMMARY

In general, in one aspect, one or more embodiments disclosed herein relate to a clinical information management system comprising: a patient sensor system that collects data of a patient; a patient monitoring system that displays the data; a clinical server that processes the data from the patient sensor system and determines whether the patient is in need of assistance; and based on the data, the clinical server transmits a message to the patient monitoring system.

In another aspect, one or more embodiments disclosed herein relate to a clinical information management method comprising: determining that a patient is interfacing with a sensor array; scanning the sensor array periodically to collect data from the patient; processing the data using algorithms stored in a computer-readable medium; transmitting a message, based on processed data, to a patient monitoring system.

Other aspects and advantages of the invention will be apparent from the following description and the appended claims.

DETAILED DESCRIPTION

Figure 1A:
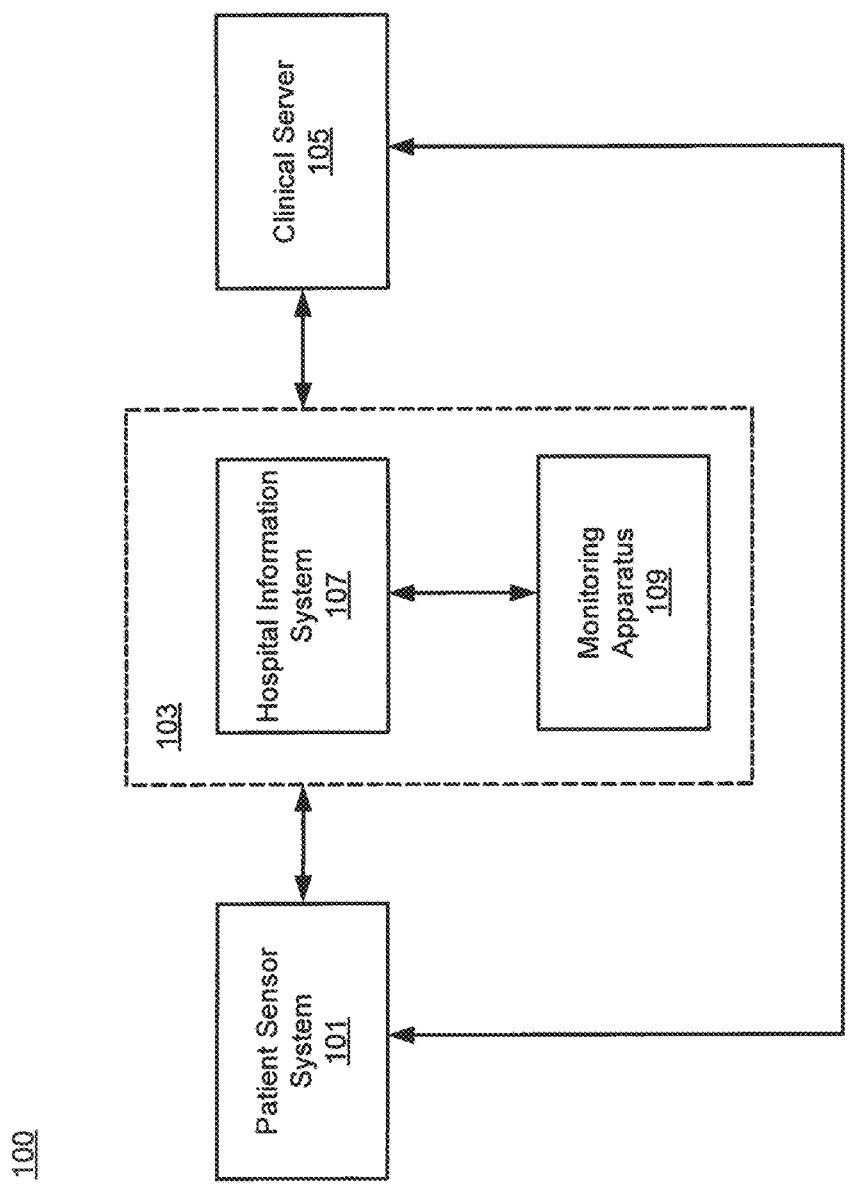
FIG. 1A shows a clinical information management system according to one or more embodiments of the invention.

Specific embodiments will now be described in detail with reference to the accompanying figures. Like elements in the various figures are denoted by like reference numerals for consistency. Like elements may not be labeled in all figures for the sake of simplicity.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create a particular ordering of the elements nor to limit any element to being only a single element unless expressly disclosed, such as by the use of the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a component surface" includes reference to one or more of such surfaces. Furthermore, it is to be understood that the term "or" may or may not be inclusive, unless the context clearly dictates otherwise.

The inventors recognize that doctors, nurses, and other healthcare workers are scarce resources. To maximize patientcare without compromising the quality of care, one or more embodiments of the invention organize and streamline tasks so that healthcare workers can do their jobs more efficiently and accurately when caring for patients.

One or more embodiments of the invention relate to a clinical information management system and method. The clinical information management system and method may be deployed in a healthcare facility (e.g., hospital, clinics, etc.) to better assist healthcare providers in providing care for their patients.

Advantageously, one or more embodiments of the invention relate to providing patient physiological information in real-time, providing visual management interface that allows healthcare workers to quickly comprehend patient statuses, monitoring the quality of care provided by healthcare workers, prioritizing patient needs and sending warning messages to healthcare workers so that timely actions may be taken by healthcare workers to assist patients, storing patient data and extrapolating/predicting patient behavior, analyzing patient data trends, and providing a communication platform to enable healthcare workers to collaborate with one another.

FIG. 1 shows a clinical information management system (100) according to one or more embodiments of the invention. As shown in FIG. 1, the system (100) comprises multiple subsystems and components, including a patient sensor system (101), a patient monitoring system (103), and a clinical server (105). The various subsystems and components of the system (100) may communicate directly or indirectly with one another. The means for communicating such information is not limited and may be at least one selected from the following interfaces: Local Area Network (LAN), Wide Area Network (WAN) or the Internet through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can also be established using a variety of communication protocols (e.g., TCP/IP, IPX, SPX, NetBIOS, Zigbee, Bluetooth, Ethernet, ARCNET, SONET, SDH, Fiber Distributed Data Interface (FDDI), RS232, RS485, IEEE 802.11, IEEE 802.11a, IEEE 802.11b, IEEE 802.11g, CDMA, GSM, WiMax and direct asynchronous connections).

The communication may be exchange of information, storage of information, etc. The information within the system (100) described herein may be stored in one or more data structures. Further, any data structure type (e.g., arrays, linked lists, hash tables, etc.) may be used to organize information within the data structure(s) provided that the data structure type(s) maintain the various exchange of information described.

Interactions among the various parts of the subsystems of the system (100) may be described as follows: A patient interfaces with a patient sensor system (101). The patient sensor system (101) collects data regarding the patient and transmits the data to the patient monitoring system (103) or the clinical server (105). The data is processed at the clinical server (105) and then displayed on the patient monitoring system (103). For the purposes of this application, the term "interface" means that a user is using a sensor apparatus in its intended form. As will be described in detail below, a user may interface with a pressure sensing device, for example, by lying on the device, thereby exerting pressure on the pressure sensing device. For example, a user may interface with an underwear sensor that calculates menstrual cycle by wearing the underwear comprising the underwear sensor. Each of the subsystems and components of the system (100) is now described in detail.

The patient sensor system (101) may be a device or apparatus that receives physiological signs, postures, movements, etc., from a patient using one or more sensors embedded in the device or apparatus. The physiological signs may include, but are not limited to, body temperature, pulse rate, respiration rate (rate of breathing), blood pressure, etc. The sensor for making such measurements may include a pressure sensor that measures the amount of pressure exerted by the patient. The sensor may be a thermometer that measures patient temperature. The sensor may be a heart monitor that measures pulse rate. The sensor may be a pedometer that records the number of steps walked. The sensor may be a gyroscope that determines an orientation. The sensor may be a g-sensor that measures acceleration force as well as determines center of mass. The g-sensor may be an accelerometer. Different scenarios and examples of the usage of the patient sensor system (101) are described in more details below in conjunction with FIG. 3.

The device or apparatus of the patient sensor system (100) may be a wearable one, like a watch. The device or apparatus may be implanted into an underwear, a sock, etc. The device or apparatus may be a non-wearable one, like a mattress. One of ordinary skill in the art would appreciate that the device or apparatus may include a transmitter, a receiver, and a memory. One of ordinary skill in the art would appreciate that the device or apparatus may be implemented by circuits, processors, etc., using any known methods. For example, the processor may be an integrated circuit for processing instructions. For example, the processor may be one or more cores, or micro-cores of a processor. For example, the memory may be random access memory (RAM), cache memory, flash memory, etc.

As discussed above, the form and shape of the specific sensors that make up the patient sensor system (101) are not limited and vary depending on the parameters to be measured. The primary functions of the patient sensor system (101) are to extract data from patients and transmit the same to either the patient monitoring system (103) for display or the clinical server (105) for further processing. The patient sensor system (101) itself may or may not comprise the means for processing raw data collected as a result of interfacing with patients.

According to one or more embodiments of the invention, the patient sensor system (101) may be a separate apparatus or device of its own or may be a part of a bigger system disposed in a patient's hospital room. Accordingly, for example, the patient sensor system (101) may further comprise a call button that enables the patient to contact a healthcare worker when in need of help. For example, the patient sensor system may further comprise a display and other peripheral components.

The patient monitoring system (103) receives the sensor data transmitted from the patient sensor system (101) and the clinical server (105) and displays corresponding patient data visually so as to enable healthcare workers to monitor patient health status. The patient monitoring system (103) may be a hospital information system (107) at a nurse station (areas in a healthcare facility, such as a hospital, clinic, nursing, etc., where nurses centralize patient monitoring and ward administration.). Nurse stations (107) are often located at the center of wards near patient rooms, so as to facilitate the ward administration and allow patients, accompanying families and visitors to receive assistance from nurses. In some hospitals, the nurse station is a closed-type space that is similar to an office, while in other hospitals, the nurse station may be an open-type space such as a counter with a semicircular, waist-high work bench. Often, nurse stations have a physical white board for manually recording patient status and test results as well as recording the medical attendants' schedule and notices related to the patients in order to constantly display and remind patient requirements.

The patient monitoring system (103) may be a portable monitoring apparatus (109). The monitoring apparatus (109) may be any device having a display. For example, the monitoring apparatus (109) as a watch is discussed in more detail in conjunction with FIGS. 5A-5L. One aspect that the monitoring apparatus (109) differs from the hospital information system (107) is that the monitoring apparatus (109) is portable and lean.

One of ordinary skill in the art would appreciate that the patient monitoring system (103) may be a desktop personal computer (PC), a laptop, a tablet, an electronic reader (e-reader), a cable box, a kiosk, a smartphone, a server, a mainframe, a personal digital assistant (PDA), or any other type of hardware device. Each hardware device, other than having the display, may further include a processor, persistent storage, and a memory to execute the one or more applications (103 A, 103 N). As with the subcomponents of the system (100), the hardware device may communicate (directly or indirectly) with one another, with the clinical server (105), or the patient sensor system (101) using any wired or wireless (e.g., wifi, cellular, etc.) connections. Further, each of the hardware device of the patient monitoring system (103) may also include one or more input device(s), such as a touchscreen, keyboard, mouse, microphone, touchpad, electronic pen, or any other type of input device. Furthermore, the display of the hardware device may be a screen (e.g., a liquid crystal display (LCD), a plasma display, touchscreen, cathode ray tube (CRT) monitor, projector, or other display device. The hardware device may also include a printer, external storage, or any other output device. One or more of the output devices may be the same or different from the input devices. Many different types of computing systems exist, and the aforementioned input and output devices may take other forms.

The clinical server (105) receives, processes, and transmits sensor data from the patient sensor system (101) or the patient monitoring system (103). The clinical server (105) may be disposed in the same hospital housing the hospital information system (107) or may be disposed at a separate location. The clinical server (105) may be affiliated with the same entity as the hospital information system (107) or may be provided by a third-party affiliate. That is, the third-party affiliate may maintain a server that receives, processes, stores, and transmits the sensor data on behalf of the hospital. The clinical server (105) may be any server using any platform. One of ordinary skill in the art would appreciate that a server is a computer program or device that provides functionality for other programs or devices (i.e., clients). The server distributes computations across multiple processes or devices for efficiency.

Those skilled in the art will appreciate that while FIG. 1A shows a particular system configuration, the disclosure is not limited to the aforementioned system configuration.

Figure 1B:
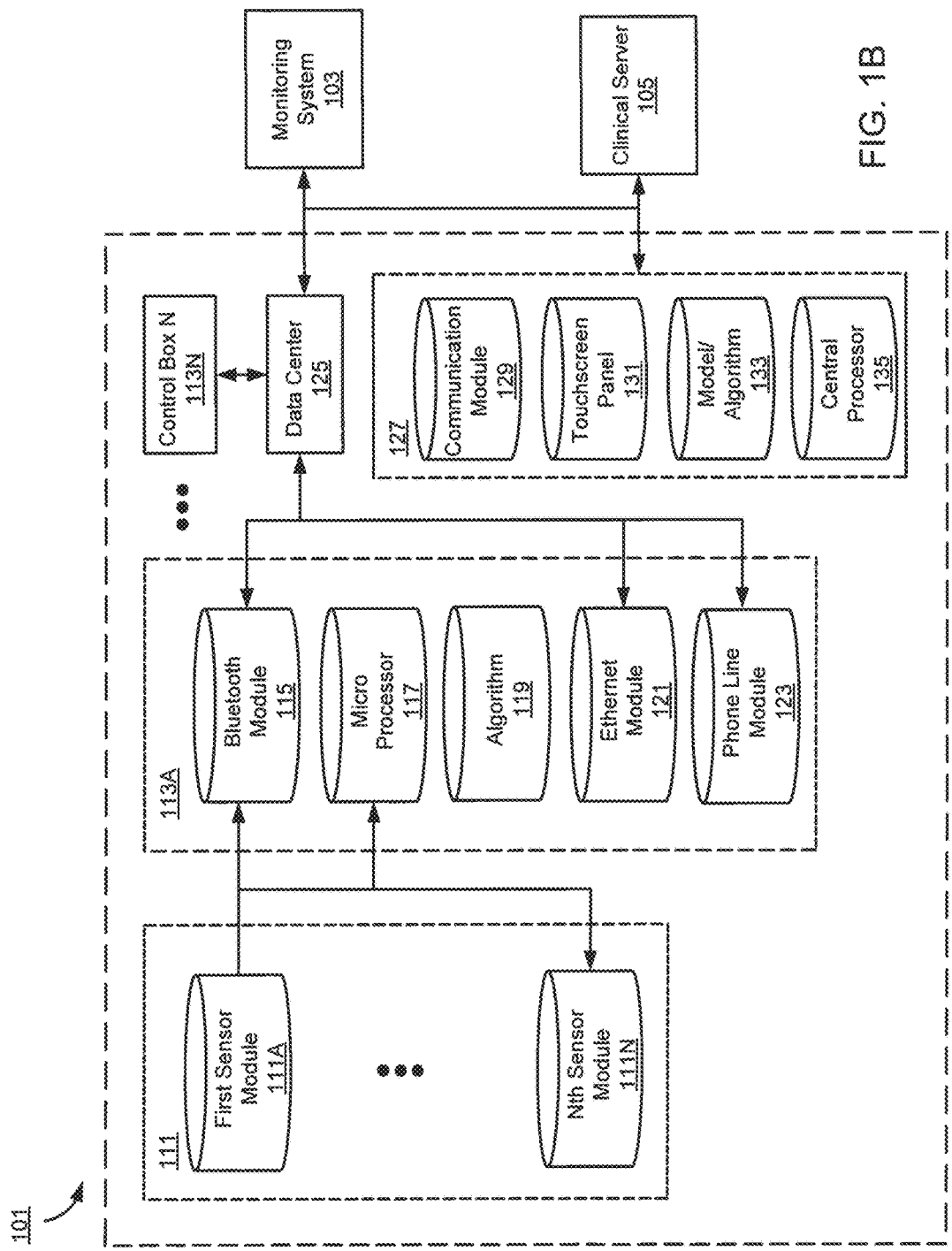
FIG. 1B shows a clinical information management system according to one or more embodiments of the invention.

FIG. 1B shows a clinical information management system according to one or more embodiments of the invention. More specifically, FIG. 1B shows an example of the components making up the patient sensor system (101).

The patient system sensor (101) may comprise sensors (111) grouped into one or more sensors arrays (101A, 101N), one or more control boxes (113A, 113N), a data center (125), and a central control system (127).

As discussed above, the sensors (111) may be disposed on wearable or non-wearable devices. Furthermore, as discussed above, the sensors may be of any shape, size, and formation.

The one or more control boxes (113A, 113N) may each comprise a Bluetooth module (115), a processor (117), one or more executable algorithms (119) stored on a non-transitory storage medium, an Ethernet module (121), a phone line module (123).

The one or more control boxes (113A, 113N) are operatively connected to the sensors (111). And, upon receiving data from the sensors (111), the one or more control boxes may process the same using the algorithms (119) and the processor (117). Furthermore, the one or more control boxes (113A, 113N) may transmit the processed/unprocessed data from the sensors (111) to the data center (125) via Bluetooth (using the Bluetooth module (115)), Ethernet cable (using the Ethernet module (121), or the phone line (using the phone line module (123)).

Upon receipt of the data, the data center (125) may transmit the same to the patient monitoring system (103) or the clinical server (105) for further processing.

Alternatively, or in addition to the above, the data center (125) may transmit to the central control system that in turn transmits to the patient monitoring system (103) and the clinical server (105).

In the central control system (127), the communication module (129) enables transmission of data between the central control system (127) and the clinical server (105) and the patient monitoring system (103). The specific mechanism for doing so is not limited and may include anything ranging from Bluetooth to phone line module, using any known standards. The touchscreen panel (131) is configured to allow a user of the patient sensor system (101) to provide input, including sending an emergency request, a meal request, etc., such that he is able to communicate directly with the patient monitoring system (103) or the clinical server (105). Furthermore, the touchscreen panel (131) may be provided to allow the patient to dim the light of the room, to switch channel on a television, to place a phone call, etc. The model/algorithm (133) is stored on a non-transitory storage medium. The model/algorithm (133) works in conjunction with the central processor (135) to process the data received from the sensors (111). As shown in FIG. 1B, the data obtained from the sensors (111) may first be processed by the algorithm (119) and, successively, by the model/algorithm (133). Advantageously, by dividing a model into a plurality of pieces and storing the same into separate hardware components, additional steps are taken to prevent manufacturers from intentionally or unintentionally disclosing algorithms.

Figure 1C:
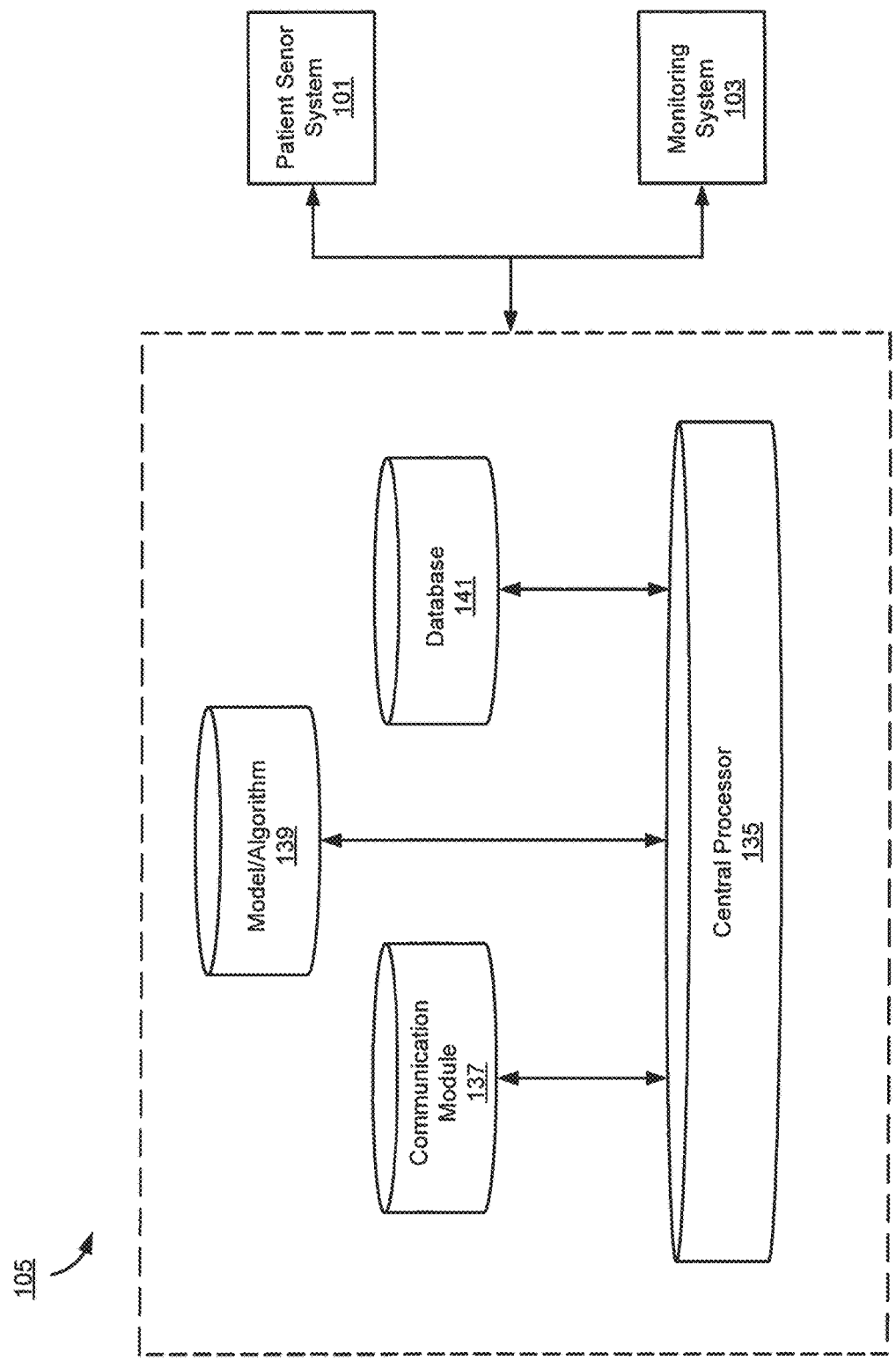
FIG. 1C shows a clinical information management system according to one or more embodiments of the invention.

FIG. 1C shows a clinical information management system according to one or more embodiments of the invention. More specifically, FIG. 1C shows an example of the components making up the clinical server (105).

The clinical server (105) may comprise a communication module (137), a model/algorithm (139) stored on a non-transitory storage medium, and a database (141). As with the communication module (129), the communication module (137) can be implemented using any known method. As with the model/algorithm (133), the model/algorithm (139) is stored on a non-transitory storage medium and processes data obtained from the sensors (111). The database (141) comprises patient historical data and adjusts thresholds and other parameters tailoring to a particular patient. According to one or more embodiments, the server (105) may transmit adjusted thresholds or other parameters based on the patient data to the central control system (127) or one or more control boxes (113A). And while the clinical server (105) may be comprise of local servers stored in a local datacenter facility, it may also be a cloud server. Cloud server is used to perform cloud computing, which is a kind of network-based computing that provides shared processing resources and data to computers and other devices on demand. The cloud server utilized by the present invention may be a private cloud, which is a cloud infrastructure operated solely for a single organization, a public cloud, or a hybrid cloud. Public cloud is rendered over a network that is open for public user. Hybrid cloud is a composition of two or more clouds. Other deployed cloud architectures in the present invention may include, for example, a community cloud that shares infrastructure between several organizations, a distributed cloud that assembles a platform ranging from machines in different locations, an intercloud (also known as cloud of clouds), and a multicloud that uses multiple cloud computing services in a single heterogeneous architecture to reduce reliance on a single vendor.

Figure 2:
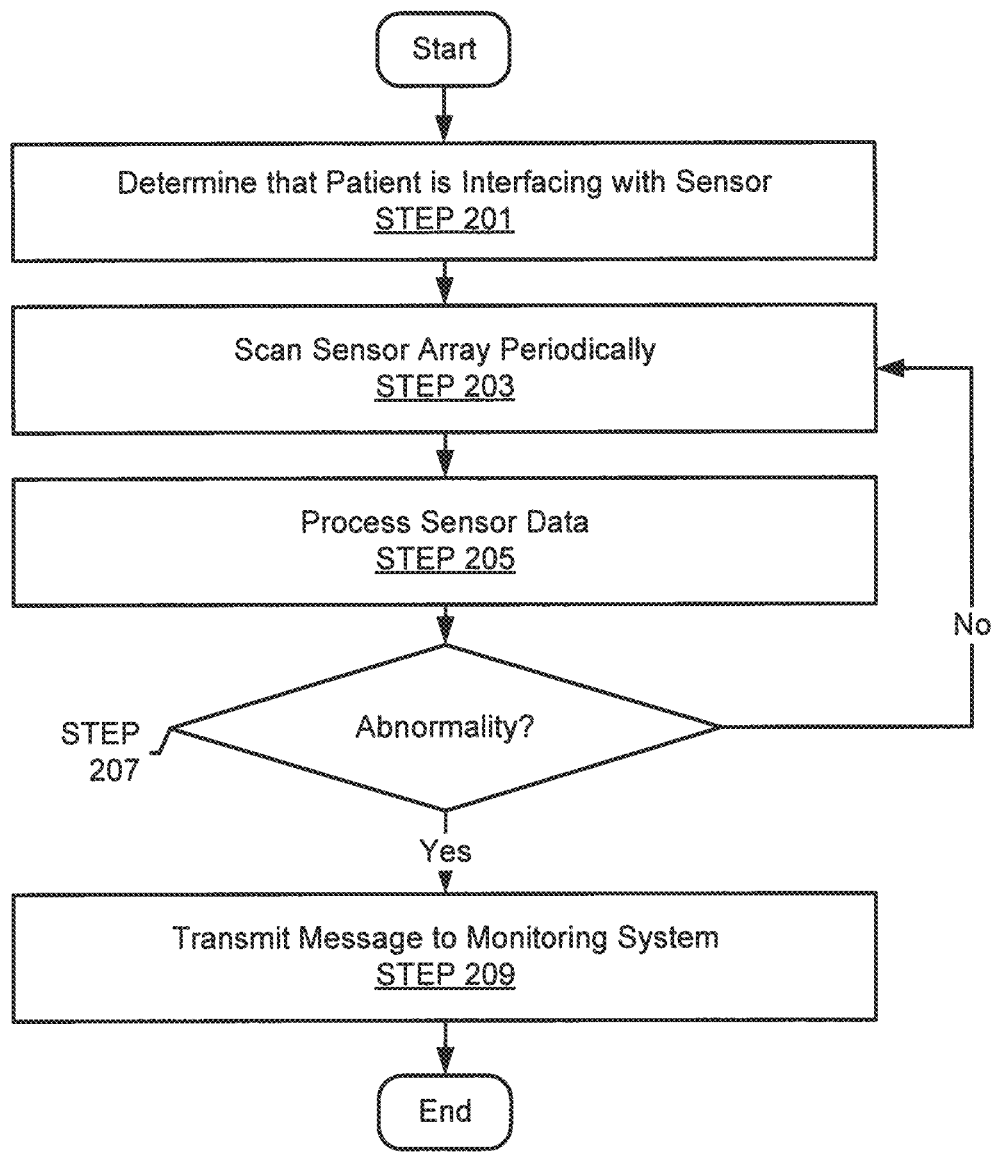
FIG. 2 shows an example of a clinical information management method according to one or more embodiments of the invention.

FIG. 2 shows an example of a clinical information management method according to one or more embodiments of the invention. Although the method is illustrated as a flowchart having steps that are described sequentially, one of ordinary skill in the art would appreciate that some or all of the steps may be executed in different orders, may be combined or omitted, and some or all of the steps may be executed in parallel.

In Step 201, a determination is made as to whether a patient is interfacing with a patient sensor system (101). The ways in which the patient interfaces with the patient sensor system (101) may differ based on the nature of the sensor and the data sought to be collected by the patient sensor system (101). For example, a pressure sensor of the patient sensor system may be embedded in a pad of a hospital bed to determine whether a patient is lying on the bed. If the patient is not interfacing with the sensor (i.e., not lying on the bed), the patient sensor system (101) may be put into a hibernation mode so as to preserve battery power or to reduce energy consumption.

One other example in which the patient sensor system determines that the patient is interfacing with the sensor may be when the patient interfaces with a touch screen (which could be temperature-based, capacitive based, etc.). If the patient is not interfacing with the sensor (i.e., not touching the touch screen) for a predetermined amount of time, the patient sensor system (101) may be put into a hibernation mode thereby displaying, via a display of the patient sensor system (101), a screensaver.

One other example in which the patient sensor system determines that the patient is interfacing with the sensor may be when a g-sensor/accelerometer—sewn into a sock—determines the patient's change in orientation, center of mass, pace (walking rate and speed), etc. If the patient is not interfacing with the sensor (i.e., not walking, not changing orientation, not accelerating, etc.) for a predetermined amount of time, the patient sensor system (101) may be put into a hibernation mode so as to preserve battery power or to reduce energy consumption.

In Step 203, sensors or sensor arrays are periodically scanned to record data. For the purposes of this disclosure, sensor array is a group of sensors deployed in a certain geometry pattern used for collecting and processing signals. The sensors themselves may be of any geometric shape including, but not limited to hexagonal, square, rectangular, circular, etc. These sensors may in turn be grouped into a pattern with no limitation to the particular shape. Furthermore, based on the particular data sought to be obtained from the patient, the shapes of the sensors and the arrangement of the sensors may differ. For example, because a human limb is generally lighter than a human torso, the sensors for detecting limb pressure may be more sensitive than the sensors for detecting torso pressure. To achieve more sensitive detections, more numerous sensors may be used or sensors having higher resolutions may be used.

In Step 205, upon receiving the data collected by the sensors or the sensor arrays, a clinical server (105) processes the data. However, as discussed above, the clinical server (105) may be monolithic to the hospital information system (107) or the monitoring apparatus (109). Said in another way, the data processing may take place not at the clinical server (105), but at the hospital information system (107) or the monitoring apparatus (109). By sorting the data in view of built-in algorithms stored in memory, the clinical server (105) determines whether there is abnormality in the data. For example, based on the received pressure sensor data, the clinical server (105) may determine that the patient is lying close to an edge of his or her bed and is in danger of falling off the bed. For example, based on the received pressure sensing data, the clinical server (105) may determine that a patient has not rolled his or her body in a predetermined amount of time and may require assistance to improve blood circulation. For example, based on the received pressure sensing data, the clinical server (105) may determine whether the patient is placed in Fowler's position (low, semi, standard, high Fowler's, low Fowler's, etc.). For example, based on the received g-sensor/accelerometer data, the clinical server (105) may determine whether a patient has fallen, tripped, etc.

The flowchart returns to Step 203 to continue scan patient's interfacing with the patient sensor system (101) if there is no abnormality detected in Step 205. If there exists abnormality based on predetermined threshold, the flowchart proceeds to Step 209.

In Step 209, a warning message is sent to the clinical server (105) or the patient monitoring system (103)—which includes the hospital information system (107) and the monitoring apparatus (109)—indicating causes of the abnormality determined in Step 207. For example, the warning message may read "Patient Leaving Bed." For example, the warning message may read "Need Your Help." For example, the warning message may read "Patient Fallen." However, one of ordinary skill in the art would appreciate that even if Step 207 does not determine patient abnormality, the processed data may be transmitted to and displayed on the hospital information system (107) or the monitoring apparatus (109). For example, regardless of findings of abnormality, a patient's heart rate may be transmitted and viewed by a healthcare worker using the hospital information system (107) or the monitoring apparatus (109). According to one or more embodiments, a second warning message may be sent to a second monitoring apparatus if the monitoring apparatus (109) does not respond to the warning message.

Figure 3:
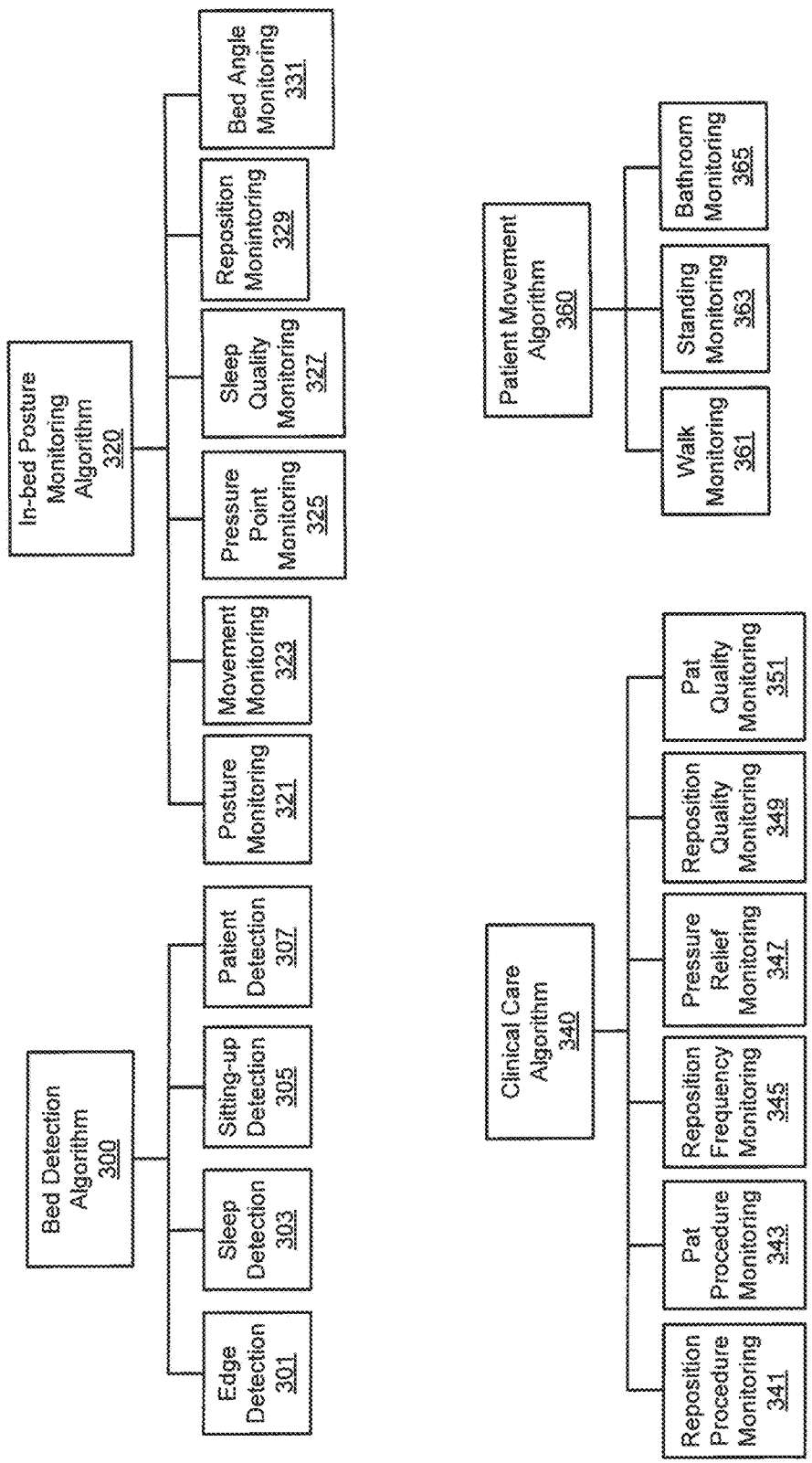
FIG. 3 shows various algorithms according to one or more embodiments of the invention that may be implemented by the clinical information management system or the clinical information management method of FIGS. 1 and 2.

FIG. 3 shows various algorithms according to one or more embodiments of the invention that may be implemented by the clinical information management system or the clinical information management method of FIGS. 1 and 2.

Bed Detection Algorithm

The bed detection algorithm (300) determines a patient's behavior in bed. By placing pressure sensors on the bed, the bed detection algorithm is able to determine the patient's position on the bed. The bed detection algorithm (300) is a generic term that includes many algorithms for detecting the patient. The bed detection algorithm (300) may include edge detection (301), sleep detection (303), sitting-up detection (305), patient detection (307), etc.

In edge detection (301), by dividing the bed into ten equal vertical sensing zones and detecting only pressure from the rightmost tenth sensor zone, for example, the clinical information management system may determine that the patient is about to fall off from the right side of the bed.

In sleep detection (303), the bed may be portioned into different detection zones as in edge detection (301). The clinical information management system may determine that the patient is asleep if the various zones receive relatively constant pressure from the patient (i.e., the amount of pressure exerted by the patient on the detection zone is relatively constant). On the other hand, if the pressure exerted by the patient is constantly changing, it may be that the patient is constantly stirring on the bed and either in light sleep or in an awaken mode.

In sitting-up detection (305), by dividing the bed into three equal horizontal sensing zones and detecting high pressure on the top third detection zone, low pressure on the middle third detection zone, and no pressure on the bottom third detection zone, for example, the clinical information management system may determine that the patient is in a sitting position.

In patient detection (307), the clinical information management system may be able to determine whether the patient is on the bed or about to leave the bed by determining whether there is pressure and the amount or the distribution of pressure exerted on the pressure sensor. Alternatively, motion sensor may be coupled to the bed to determine whether the patient is present.

In-bed Posture Monitoring Algorithm

The in-bed posture monitoring algorithm (320) monitors a patient's posture in bed. By placing pressure sensors on the bed, the in-bed posture monitoring algorithm is able to monitor the patient's posture on the bed. The in-bed posture monitoring algorithm (320) is a generic term that includes many algorithms for detecting the patient posture. The in-bed posture monitoring algorithm (320) may include posture monitoring (321), movement monitoring (323), pressure point monitoring (325), sleep quality monitoring (327), reposition monitoring (329), bed angle monitoring (331).

In posture detection (321), the bed is portioned and provided with pressure sensors at each of the portions. By determining how much pressure is being exerted on each of the portioned bed and the amount of contact between the body and the bed, the clinical information management system is able to monitor the posture (e.g., back sleepers, side sleepers, stomach sleepers, etc.) of the patient in bed.

In movement monitoring (323), the algorithm monitors whether the patient is moving on the bed using sensors disposed at various portions of the bed. The algorithm may determine the patient is at a high risk of ulcer if the patient is not moving beyond a predetermined period of time.

In pressure point monitoring (325), the algorithm monitors specific areas of contact between the patient and the bed. This is to facilitate the healthcare worker in determining whether the patient has sufficient blood circulation either locally or otherwise. For example, patients may have peripheral artery disease, which can lead to poor circulation in legs by causing narrowing of the blood vessels and arteries. Another way for determining pressure point may be to calculate the geometric center of gravity of body torso and monitor the pressure point of the torso area. Furthermore, the pressure point monitoring (325) may be used to prevent ulcer.

In sleep quality monitoring (327), a patient's sleep quality may be tracked. One type of sensor for detecting patient sleep may be a microphone for recording and analyzing snores, body movement, etc. In another type of sensor for detecting patient sleep may be an eye tracker that determines rapid eye movement. In another type of sensor for detecting sleep may be a motion sensor that detects and record the patient's movement during sleep.

In reposition monitoring (329), pressure sensor is configured to determine pressure exerted on a particular area of the senor arrays from a particular location of the patient's body. In particular, by providing a mapping of an amount of pressure as a function of time from a particular location of the patient's body, the hospital information management system and method are more easily able to monitor whether healthcare workers are providing the quality of care of needed by the patient. A reposition reminder may be transmitted to the hospital information management system or the monitoring apparatus if the amount of pressure on a particular area of the sensor arrays has not changed beyond a predetermined period of time.

In bed angle monitoring (331), the tilt angle of the bed may be fed to the clinical information management system.

Clinical Care Algorithm

The clinical care algorithm (340) measures the quality of care provided by healthcare workers by using one or more types of sensors (including camera, gyroscope, g-sensor/accelerometer, and pressure sensing mats). The clinical care algorithm (340) is a generic term that includes many algorithms for determining the quality of care provided by healthcare workers. The clinical care algorithm (340) may include reposition procedure monitoring (341), pat procedure monitoring (343), reposition frequency monitoring (345), pressure relief monitoring (347), reposition quality monitoring (349), and pat quality monitoring (351).

The reposition procedure monitoring (341) records how the healthcare worker repositions a patient on bed (i.e., from his back to his stomach, and vice versa.). The reposition procedure monitoring (341) records the healthcare worker repositioning a patient on bed. The video may be compared to be standard operating procedure using computer vision techniques. A g-sensor may be used to collect data with respect to the reposition performed by the healthcare worker by detecting change of the pressure or evolution of such change.

The pat procedure monitoring (343) records how the healthcare worker pats a patient on his or her back. The pat procedure monitoring (343) may be implemented similar to the reposition procedure monitoring (341).

The reposition frequency monitoring (345) is directed to tracking the number of time that a healthcare worker performs reposition on a patient over a period of time. The reposition frequency monitoring (345) may be determined by using a g-sensor/accelerometer, a gyroscope or combination thereof. For example, by implanting or embedding a gyroscope into a wearable article worn by the patient, the number of reposition taken by the patient may be counted. For the purpose of this application, reposition may consist of a roll of the patient's body considered a single 360° rotation about an axis parallel to a height of the patient. Thus, for example, if the patient rotates 7,560° in a span of 5 hours, the gyroscope may transmit data to the patient monitoring system indicating that the patient has been rolled 21 times. Other data may be transmitted, including the number of rolls per hour, a log indicating the time of each roll, etc. A g-sensor may be used to collect data recording the reposition.

The pressure relief monitoring (347) is directed to recording and analyzing the amount of pressure being exerted on a particular area of the sensor arrays from localized points of the patient. For example, one pressure point might be a particular point on a patient's leg; another pressure point might be a particular point a patient's arm. The pressure point monitoring (347) may be implemented using a pressure sensor. By determining the amount of pressure being exerted on a particular area of the sensor arrays from a particular location over a period of time, the healthcare worker would be able to determine how best to mobilize the patient to prevent ulcer.

The reposition quality monitoring (349) compares the video recorded of the healthcare worker performing the reposition to a standard reposition procedure. The reposition quality monitoring (349) then determines whether the healthcare worker's performing the reposition on the patient is acceptable in view of the standard reposition procedure. Alternatively, or in addition to the above, the reposition quality monitoring (349) may be completed by using a g-sensor/accelerometer, a gyroscope or combination thereof. The g-sensor/accelerometer is used to measure acceleration forces, which is the measurement of the change in velocity. The gyroscope, as discussed above, measures orientation. The combination of the two would yield insight into how quickly the healthcare worker is turning the patient. Caution should be taken in caring for patients. An acceleration too great whilst repositioning the patient may cause discomfort. For example, if the measured angular acceleration associated with a revolution exceeds a predetermined angular acceleration, the monitoring system may be sent a warning message.

The pat quality monitoring (351) is similar to the reposition quality monitoring (349), but directed to determining the quality of pat provided by the healthcare worker to the patient. The pat quality monitoring (351) may be implemented using a pressure sensor to determine the number of pats the healthcare worker has given to the patient. Alternatively, or in addition to the above, the pat quality monitoring (351) may be performed by detecting the change in the amount of pressure being asserted on, for example, a pressure sensing mat. Because the pressure sensor is able to determine sudden changes in exerted pressure, when a healthcare worker pats the patient lying on the pressure sensor, the pressure sensor detects the change in pressure. A count of such pressure changes may be recorded. And, if the count falls below a predetermined threshold, the monitoring system may be sent a warning message.

Patient Movement Algorithm

The patient movement algorithm (360) measures a patient's movement in general. The patient movement algorithm (360) may include walk monitoring (361), standing monitoring (363), and bathroom monitoring (365).

In walk monitoring (361), the pace, the stride, the direction, and the center of mass of the patient may be tracked using GPS technology, g-sensor/accelerometer, etc. A warning message may be transmitted if an abnormal or disordered gait is detected.

In standing monitoring (363), the stance, the center of mass, and the posture of the patient may be tracked by disposing wearable sensors on the patient's clothes.

In bathroom monitoring (365), the amount of time spent in the bathroom may be tracked. Additional information pertinent to bathroom usage may be tracked (the specific types of data collected vary depending on the jurisdiction and its data privacy laws). For example, a pH meter may be installed in a toilet for interfacing with the patient. The pH reading of the patient's urine may be determined and transmitted to the clinical information management system.

One of ordinary skill in the art would appreciate that one or more algorithms and their sub-algorithms may be combined depending on the specific data sought to be collected by the clinical information management system.

Figure 4:
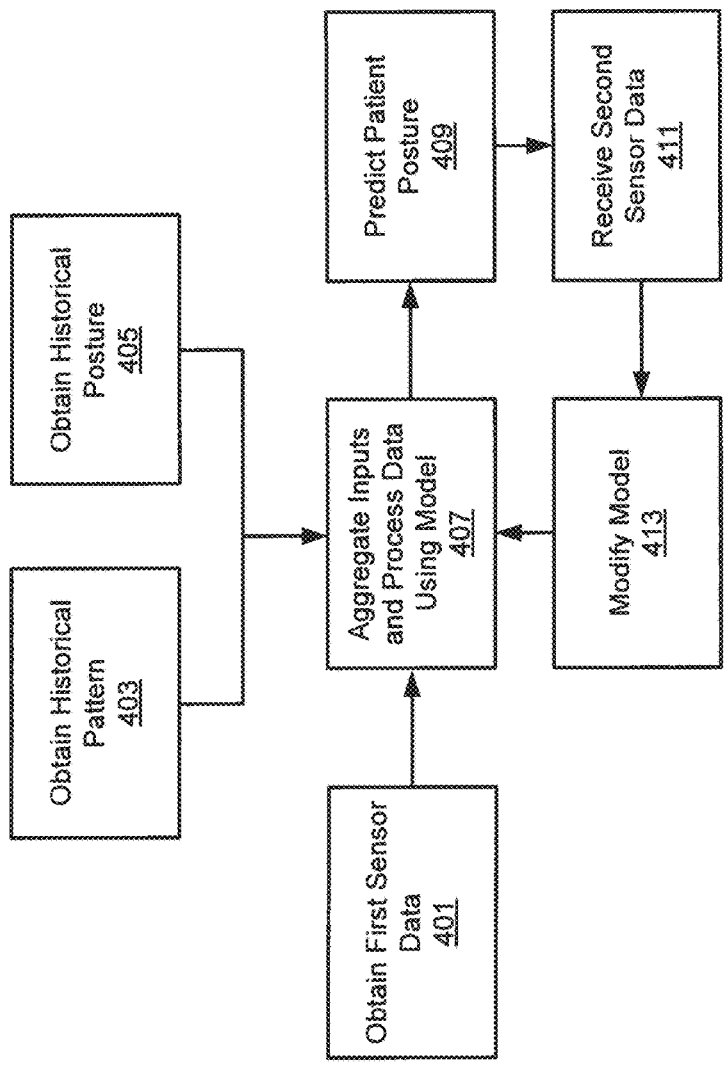
FIG. 4 shows an algorithm for predicting patient posture according to one or more embodiments of the invention.

FIG. 4 shows a self-learning model that modifies the algorithms in FIG. 3 based on the patient's data. This enables specific warnings to be set/tailored towards specific patients (e.g., an abnormally high heart rate for one person may be the norm for another). Data from patient is useful in modifying existing algorithms and for predicting future behavior for the patient. Thus, FIG. 4 also shows an algorithm for predicting patient posture according to one or more embodiments of the invention.

Patient posture can be determined as described in reference to FIG. 3. One or more embodiments of the invention also relate to predicting patient posture based on historical data. By leveraging historical data, the various algorithms of the clinical information management system may be configured to refine itself in determining what constitutes the norm.

In Step 401, a first sensor data from patient A is collected.

In Steps 403 and 405, sensor data pertaining to historical pattern and historical posture for the entire data set (e.g., patients B-Z) are imported.

In Step 407, patient A's data is calibrated in view of the historical pattern and the historical posture.

In Step 409, patient A's posture is predicted.

In Step 411, a second sensor data from patient A is collected.

In Step 413, if the second sensor data differs drastically from the prediction made in Step 409, the model of Step 407 is modified. If the second sensor data conforms to the prediction, the second sensor data is stored as part of the historical pattern and the historical posture.

FIGS. 5A-5L show user interfacing with an example monitoring apparatus according to one or more embodiments of the invention. For the purposes of illustration only, the monitoring apparatus in FIGS. 5A-5L takes the form of a watch.

Figure 5B:
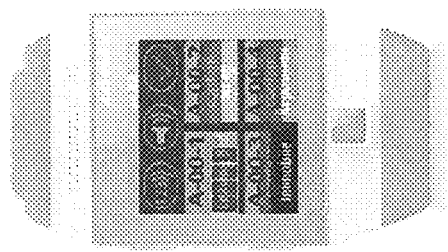
FIGS. 5A-5L show user interfaces of an example monitoring apparatus according to one or more embodiments of the invention.
Figure 5D:
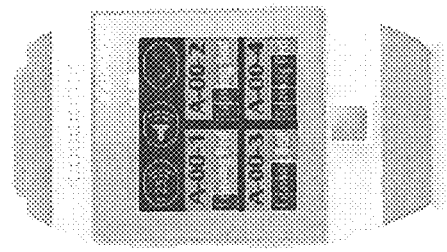
Figure 5A:
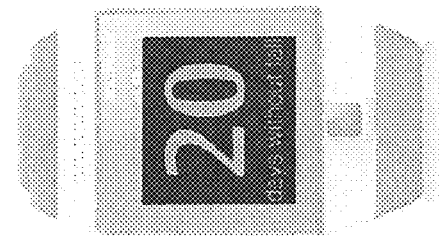

FIG. 5A shows a watch indicating that the patient has been tracked for 20 days and the patient has not fallen in each of the 20 days.

FIG. 5B shows a watch used by Nurse A. The watch shows 4 patient statuses (including patient A-00-1, A-00-2, A-00-3, and A-00-4). As shown in A-00-1, the 4 equally portioned bars are solid in color (indicating that the user is on the bed and has not left) and the patient is away from the bed. Other marks for tracking whether the patient is or is not on the bed may be used and can vary depending on the specific arrangement of the pressure sensors. Said in another way, the portioned bars may visually indicate the amount of time the patient is away from the bed or may visually indicate which portions of the bed is physically in contact with the patient. As shown in A-00-2, the nurse is asked to confirm whether the patient is in a sitting position on the bed. As shown in A-00-3, the nurse is asked to confirm whether the patient is able to walk. As shown in A-00-4, the nurse is asked to confirm whether the patient has been repositioned.

Figure 5C:
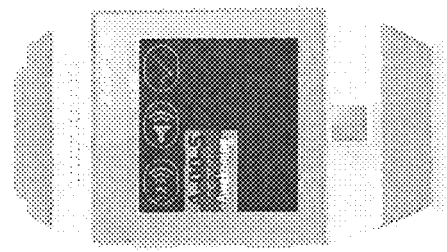

FIG. 5C shows a watch used by Nurse E. The watch shows 1 patient status. As shown in A-00-5, the nurse is asked to confirm whether the patient is awake.

FIG. 5D shows a watch used by Nurse A. The watch shows 4 patient statuses (including patient A-00-1, A-00-2, A-00-3, and A-00-4). As shown in A-00-1, there is only 1 out of 4 solid bars illuminating. This could mean that the patient is exerting pressure on only the leftmost portion of the bed or that the patient has left the bed for, for example, 15 seconds (wherein one solid represents 5 seconds). As shown in A-00-2, there are 2 out of 4 solid bars illuminating. This could mean that the patient is exerting pressure on only the two leftmost portions of the bed or that the patient has left the bed for, for example, 10 seconds (wherein one solid represents 5 seconds). As shown in A-00-3, there are 3 out of 4 solid bars illuminating. This could mean that the patient is exerting pressure on all but the rightmost portion of the bed or that the patient has left the bed for, for example, 5 seconds (wherein one solid represents 5 seconds). As shown in A-00-4, all solid bars illuminating. This could mean that the patient is exerting pressure on all portions of the bed or that the patient is on the bed.

Figure 5E:
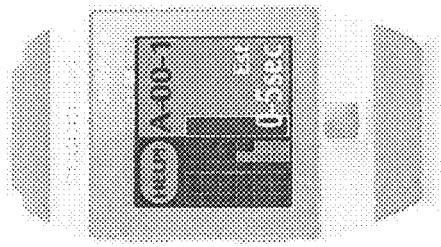

FIG. 5E shows a watch used by Nurse A. FIG. 5E shows a zoomed in view of A-00-1. Specifically, in this example, the patient has left the bed for at least 15 seconds (i.e., there is only 1 solid bar illuminating). Nurse A is presented with the option of requesting help from another healthcare worker.

Figure 5F:
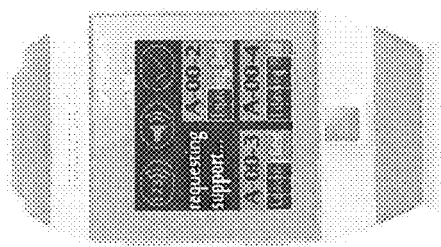

FIG. 5F shows a watch used by Nurse A. FIG. 5F shows that the nurse has indeed interfaced with the "Help" button in FIG. 5E and is now requesting help from another healthcare worker.

Figure 5G:
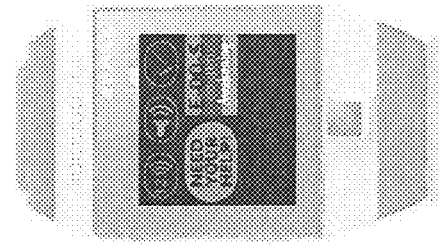

FIG. 5G shows a watch used by Nurse B. FIG. 5G shows requests from other nurses for assistance.

Figure 5H:
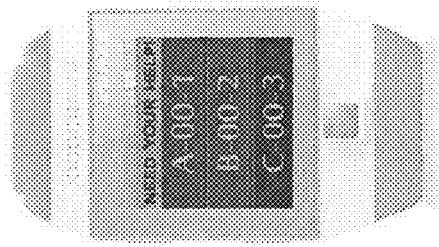

FIG. 5H shows a watch used by Nurse B. FIG. 5H shows that the patients residing on bed A-00-1 and B-00-2 require assistance.

Figure 5J:
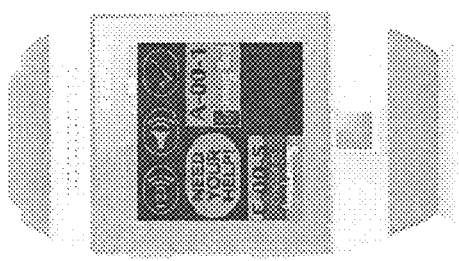
Figure 5L:
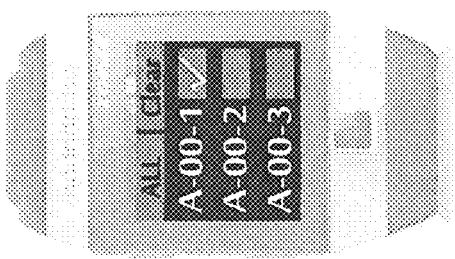
Figure 5I:
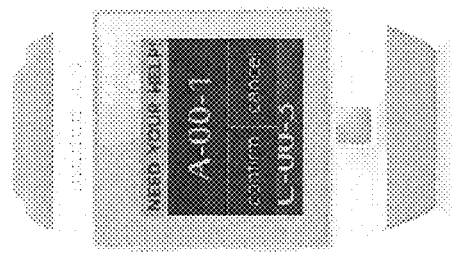

FIG. 5I shows a watch used by Nurse B. FIG. 5I shows that the nurse is requested to confirm or reject the request for help made by Nurse A.

FIG. 5J shows a watch used by Nurse B. FIG. 5J shows that the nurse has confirmed to assist Nurse A. Accordingly, the status of the patient residing on bed A-00-1 is reproduced on the screen on the watch worn by Nurse B.

Figure 5K:
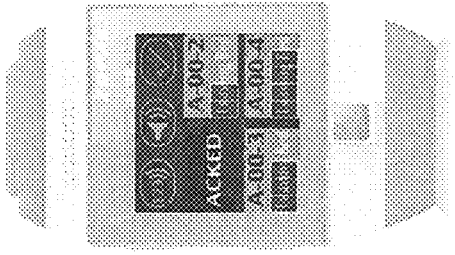

FIG. 5K shows a watch used by Nurse A. FIG. 5K shows that Nurse B has acknowledged and accepted the request by Nurse A.

FIG. 5L shows a watch used by Nurse A. FIG. 5L shows that the patient residing on bed A-00-1 has provided with the appropriate care.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A clinical information management system comprising:
a patient sensor system that collects data of a patient using a sensor array;
a clinical server that processes the data from the patient sensor system; and
a patient monitoring system that receives and displays the data transmitted from the patient sensor system or the clinical server,
wherein, based on the data, the clinical server transmits a message to the patient monitoring system, and
wherein:
the patient sensor system comprises a pressure sensor that detects and records a pat count,
the pressure sensor determines the pat count by counting a number of times in which a pressure change exceeds a predetermined threshold,
the message is transmitted to the patient monitoring system for assistance if the pat count does not exceed a predetermined pat count within a predetermined period of time.

2. The clinical information management system according to claim 1, wherein the patient monitoring system comprises at least one of a hospital information system and a monitoring apparatus.

3. The clinical information management system according to claim 2, wherein, if the monitoring apparatus does not respond to the message, a second message is transmitted to a second monitoring apparatus.

4. The clinical information management system according to claim 2, wherein the monitoring apparatus is at least one selected from a group consisting of: a watch, a smartphone, and a tablet.

5. The clinical information management system according to claim 1, wherein:
the pressure sensor comprises a pressure sensing mat that collects the data,
the pressure sensing mat is disposed in a bed, and
the message is transmitted to the patient monitoring system if the clinical server determines that, based on the data, the patient is abnormal.

6. The clinical information management system according to claim 1, wherein:
the pressure sensor comprises a pressure sensing mat that collects the data,
the pressure sensing mat is partitioned into a plurality of sections,
sensor arrays are disposed at each sections of the pressure sensing mat,
the data is patient pressure data, and
the clinical server receives the patient pressure data from each of the sensor arrays and displays, on the patient monitoring system, a video that shows the patient moving on the pressure sensing mat using the patient pressure data.

7. The clinical information management system according to claim 1, wherein the message is transmitted to the patient monitoring system when the clinical server determines that, based on the data, the patient is at a high risk of falls or ulcer.

8. The clinical information management system according to claim 1, wherein:
the patient sensor system comprises a control box that configures to processes the data using algorithms stored in a computer-readable medium,
the control box comprises a communication module that transmits the data to the clinical server, and
the clinical server, based on the data, transmits an adjusted threshold or parameter tailored for a particular patient to the control box.

9. A clinical information management system comprising:
a patient sensor system that collects data of a patient using a sensor array;
a clinical server that processes the data from the patient sensor system; and
a patient monitoring system that receives and displays the data transmitted from the patient sensor system or the clinical server,
wherein, based on the data, the clinical server transmits a message to the patient monitoring system, and
wherein:
the patient sensor system comprises a g-sensor that detects and records a quality of care provided to the patient,
the quality of care comprises a reposition frequency and a reposition procedure,
the g-sensor determines a reposition of the patient by detecting a movement of the patient along the direction of gravity,
the reposition procedure compares a g-sensor threshold with a predetermined g-sensor threshold, and
the message is transmitted to the patient monitoring system for assistance if the frequency of the reposition is below the predetermined g-sensor threshold.

10. The clinical information management system according to claim 9, wherein:
the g-sensor collects the data and is disposed on a wearable article worn by the patient,
the wearable article is at least one selected from a group consisting of: an accessory, a top, a bottom, and an underwear, and
the message is transmitted to the patient monitoring system for assistance if the clinical server determines, based on the data, that the patient is abnormal.

11. The clinical information management system according to claim 9, wherein:
the patient sensor system comprises a motion sensor that detects and records the data,
the data includes a movement signal from the patient,
the message comprises a quality of sleep of the patient, and
the quality of sleep is displayed as a number of time the patient moves during sleep.

12. The clinical information management system according to claim 11, wherein, if the monitoring apparatus does not respond to the message, a second message is transmitted to a second monitoring apparatus.

13. The clinical information management system according to claim 9, wherein the patient monitoring system comprises at least one of a hospital information system and a monitoring apparatus.

14. The clinical information management system according to claim 13, wherein the monitoring apparatus is at least one selected from a group consisting of: a watch, a smartphone, and a tablet.

15. The clinical information management system according to claim 9, wherein:
the pressure sensor comprises a pressure sensing mat that collects the data,
the pressure sensing mat is partitioned into a plurality of sections,
sensor arrays are disposed at each sections of the pressure sensing mat,
the data is patient pressure data, and
the clinical server receives the patient pressure data from each of the sensor arrays and displays, on the patient monitoring system, a video that shows the patient moving on the pressure sensing mat using the patient pressure data.

16. The clinical information management system according to claim 9, wherein the message is transmitted to the patient monitoring system when the clinical server determines that, based on the data, the patient is at a high risk of falls or ulcer.

17. A clinical information management method comprising:
determining that a patient is interfacing with a sensor array;
scanning the sensor array periodically to collect data from the patient;
processing the data using algorithms stored in a computer-readable medium; and
transmitting a message, based on processed data, to a patient monitoring system,
wherein:
the sensor is a g-sensor that detects and records a quality of care provided to the patient,
the quality of care comprises reposition frequency and a reposition procedure,
the g-sensor determines the reposition frequency by measuring acceleration and counting a number of revolutions performed by the patient, and
the message is transmitted to the patient monitoring system for assistance if the quality of care does not meet a predetermined threshold.

18. The clinical information management method according to claim 17, wherein the data is transmitted to the patient monitoring system using at least one selected from a group consisting of: an Ethernet module, a phone line module, and a Bluetooth module.

19. The clinical information management method according to claim 17, wherein the patient monitoring system comprises at least one of a hospital information system and a monitoring apparatus.

20. The clinical information management method according to claim 17, wherein:
the sensor array is disposed on a pressure sensing mat that is disposed in a bed and
the message is transmitted to the patient monitoring system if a clinical server determines that, based on the processed data, the patient is abnormal.

21. The clinical information management method according to claim 17, wherein:
the g-sensor is disposed on a wearable article worn by the patient,
the wearable article is at least one selected from a group consisting of: an accessor, a top, a bottom, and an underwear, and
the message is transmitted to the patient monitoring system if a clinical server determines that, based on the processed data, the patient is abnormal.

22. The clinical information management method according to claim 17, wherein:
the reposition procedure comprises a roll procedure that compares an angular acceleration associated a revolution with a predetermined angular acceleration, and
the quality of care does not meet the predetermined threshold if the angular acceleration exceeds the predetermined angular acceleration or if the roll count is below a predetermined roll count.

23. The clinical information management method according to claim 17, wherein:
the patient sensor system comprises a motion sensor that detects and records the data,
the data includes a movement signal from the patient,
the message comprises a quality of sleep of the patient, and
the quality of sleep is displayed as a number of time the patient moves during sleep.

24. A clinical information management method comprising:
determining that a patient is interfacing with a sensor array;
scanning the sensor array periodically to collect data from the patient;
processing the data using algorithms stored in a computer-readable medium; and
transmitting a message, based on processed data, to a patient monitoring system, wherein:
the sensor is a pressure sensor that detects and records a pat count,
the pressure sensor determines the pat count by counting a number of times in which a pressure change exceeds a predetermined threshold,
the message is transmitted to the patient monitoring system for assistance if the pat count does not exceed a predetermined pat count within a predetermined period of time.

25. A clinical information management system comprising:
a patient sensor system that collects data of a patient using a sensor array and processes the data using a control box; and
a patient monitoring system that receives and displays the data transmitted from the patient sensor system;
wherein, based on the processed data, the patient sensor system transmits a message to the patient monitoring system,
wherein the patient monitoring system comprises at least one of a hospital information system and a monitoring apparatus, and
wherein, if the monitoring apparatus does not respond to the message, a second message is transmitted to a second monitoring apparatus.

26. The clinical information management system according to claim 9, wherein:

the patient sensor system comprises a control box that configures to processes the data using algorithms stored in a computer-readable medium, the control box comprises a communication module that transmits the data to the clinical server, and the clinical server, based on the data, transmits an adjusted threshold or parameter tailored for a particular patient to the control box.

27. The clinical information management system according to claim 26, wherein the algorithms are divided into a plurality of pieces and stored into separate components of the computer-readable mediums.

* * * * *